(12) United States Patent
Zurbriggen et al.

(10) Patent No.: US 7,144,715 B2
(45) Date of Patent: Dec. 5, 2006

(54) PRODUCTION OF α-KETO BUTYRATE

(75) Inventors: Beat Denis Zurbriggen, Buelach (CH); Nadji Rekhif, Winterthur-Iberg (CH); Mara Mehlmann-De-Campos, Zurich (CH); Konrad Lerch, Pfaffhausen (CH)

(73) Assignee: Nestec S.A., Vevey (CH)

( * ) Notice: Subject to any disclaimer, the term of this patent is extended or adjusted under 35 U.S.C. 154(b) by 53 days.

(21) Appl. No.: 10/845,200

(22) Filed: May 14, 2004

(65) Prior Publication Data

US 2004/0214298 A1    Oct. 28, 2004

Related U.S. Application Data

(63) Continuation of application No. PCT/EP2002/012629, filed on Nov. 8, 2002.

(30) Foreign Application Priority Data

Nov. 29, 2001 (EP) ............................. 01128303

(51) Int. Cl.
- *C12P 1/00*  (2006.01)
- *C12P 1/04*  (2006.01)
- *C12P 21/00* (2006.01)

(52) U.S. Cl. ................ 435/170; 435/41; 435/70.1; 435/169; 435/171

(58) Field of Classification Search ................ 435/41, 435/70.1, 170, 171, 169, 196
See application file for complete search history.

(56) References Cited

U.S. PATENT DOCUMENTS 5,958,745 A    9/1999  Gruys et al. ................ 435/183
6,091,002 A *  7/2000  Asrar et al. ................ 800/288
2003/0028917 A1  2/2003  Gruys et al. ................ 800/278

FOREIGN PATENT DOCUMENTS

WO    WO 99/41395    8/1999

OTHER PUBLICATIONS

M Kisumi et al. XP002198173 "Norvaline Accumulation By Regulatory Mutants Of *Serratia-Marcescens*", Journal Of Antibiotics (Tokyo), vol. 30, No. 1, pp. 111-117, (!977).
D A Primerano et al: XP000611415 "Metabolic Basis For The Isoleucine, Pantothenate Or Methionine Requirement Of *ilvG* Strains Of *Salmonella Typhimurium*" Journal Of Bacteriology, vol. 150, No. 3, pp. 1202-1211, (1982).
Thu Thuy Pham et al. XP002198174, "Optimal conditions for the formation of sotolon from alpha-ketobutyric acid in the French "Vin Jaune"".Journal Of Agricultural And Food Chemistry, vol. 43, No. 10, pp. 2616-2619, (1995).
R A Larossa et al: XP001059085, "Toxic Accumulation Of Alpha Ketobutyrate Caused By Inhibition Of The Branched-Chain Amino Acid Biosynthetic Enzyme Acetolactate Synthase In *Salmonella-Typhimurium*", Journal Of Bacteriology, vol. 169, No. 4, pp. 1372-1378, (1987).
H. Kuwana et al: XP001059086,"The *iv-3* Mutants Of *Neurospora-Crassa* I Genetic And Biochemical Characteristics", Genetics, vol. 62, No. 3, pp. 479-485, (1969).

* cited by examiner

*Primary Examiner*—Ruth A Davis
(74) *Attorney, Agent, or Firm*—Bell Boyd & Lloyd LLC

(57) ABSTRACT

A process of obtaining α-keto butyrate by bioconversion is disclosed. The molecule is accumulated in the medium and is apt to subsequent processing to food ingredients, such as top-note flavors. A suitable strain is a natural ilv-3 mutant *Neurospora crassa* strain, which is capable of accumulating α-keto butyrate in the fermentation medium. By adjusting specific medium parameters, up to 8 g/l medium of α-keto butyrate can be accumulated.

7 Claims, 1 Drawing Sheet

PRODUCTION OF α-KETO BUTYRATE

CROSS-REFERENCE TO RELATED APPLICATIONS

This application is a continuation of International application PCT/EP2002/012629 filed Nov. 8, 2002, the entire content of which is expressly incorporated herein by reference thereto.

BACKGROUND

The present invention relates to a process for accumulating α-keto butyrate. The present invention also relates to the use of a natural mutant micro-organism and/or extracted enzyme to produce natural α-keto butyrate. The present invention also relates to a process of obtaining emoxyfurone.

Alpha-keto butyrate, a synonym of α-keto-butyric acid, 2-oxo-butyrate, 2-oxo-butyric acid, was accumulated by various organisms. According to contradictory reports, however, the molecule was also shown to be produced in balanced concentration ranges and, therefore, not to be suitable for accumulation.

In JP 03183476, it is shown that a micro-organism belonging to the genus *Pseudomonas* is capable of converting 2,3-dihydroxy butyric acid into α-keto butyric acid. However, *Pseudomonas* is not a food-grade micro-organism and, therefore, the α-keto butyric acid obtained by fermentation of this micro-organism is not easily applicable to food products. This is also valid for derivatives obtained by further processing of the α-keto butyric acid obtained by this process.

Nakahara, Nkajima-Kambe and Sato (Biotechnol. Lett. (1994), 16(3), 263–8) have shown that α-keto butyric acid can be accumulated by a *Rhodococcus equi* strain. However, in this bioconversion, 1,2-propanediol has to be added to the medium, which is not preferred for obtaining food ingredients. Additionally, it is not warranted that the micro-organism is harmless for producing food ingredients or reactants in the synthesis of food ingredients.

There are further reports of accumulation of α-keto butyric acid in recombinant micro-organisms (Kisumi, Sugiura, Takagi and Chibata, J. Antibiot. (Tokyo) 1977 Jan. 30(1), 111–7). However, for the further synthesis of flavors (food-ingredients) it is wished to get α-keto butyric acid from genetically not modified organisms.

Sluis et al (Sluis, Wolken, Giuseppin, Tramper Wijffels, "Effect of threonine, cysthionine, and the branched-chain amino acids on the metabolism of *Zygosaccharomyces rouxi*", Enzyme Microb Technol, 2000 Feb. 1; 26(2–4): 292–300) found no accumulation of α-keto-butyrate in a fungal strain, because the α-keto-butyrate pool size in this micro-organism was in balance all the time.

It was already shown that high levels of α-keto-butyrate may be toxic to a micro-organism (Fisher, Eisenstein, "An efficient approach to identify ilvA mutations reveals an amino-terminal catalytic domain in biosynthetic threonine deaminase from *E. coli*", J Bacteriol, 1993 October; 175 (20): 6605–13). In conclusion, accumulation of α-keto-butyrate may be difficult to achieve by bioconversion.

In the light of the prior art, it is an objective to obtain α-keto butyric acid in a biotechnological process. In particular, it is an objective to obtain α-keto butyric acid from a natural mutant in contrast to a genetically engineered micro-organism. In addition, a micro-organism suitable for the accumulation or production of α-keto butyric acid should be a food-grade micro-organism, in order to warrant an unobjectionable and harmless use in food-products.

In particular, α-keto butyrate is the starting point for obtaining specific furanones, for example the "Maggi-lactone" (5-ethyl-3-hydroxy-4-methy-2(5H)-furanone), which has a very strong but specific flavor and which is used in small concentrations as a "top-note". It thus would be desirable to find an alternative to the chemically synthesized α-keto butyrate that is so far used as an intermediate for further synthesis of flavors.

SUMMARY OF THE INVENTION

The present invention now provides a new process for synthesizing α-keto butyrates utilizing a micro-organism that is easy to cultivate. The resulting α-keto butyric acid is obtained from a strain by a bioconversion that does not include nutritionally questionable reactants. Remarkably, it is now possible to use a food-grade micro-organism which is a natural mutant and which accumulates and/or secretes α-keto butyric acid in sufficient amounts for use as an intermediate in the production of flavors.

In a first aspect, the present invention provides a process for accumulating α-keto-butyrate by bioconversion from threonine by a micro-organism cultivated in a fermentation medium.

In a second aspect the invention provides a process for accumulating α-keto-butyrate by bioconversion from threonine by an enzyme extract of a micro-organism.

In a third aspect the invention provides the use of a micro-organism to produce α-keto-butyrate by bioconversion from threonine.

In a fourth aspect the invention provides a process for producing 5-ethyl-3-hydroxy-4-methyl-2(5H)-furanone (emoxyfurone) or 3-hydroxy-4,5-dimethyl-2(5H)-furanone (sotolon), wherein the α-keto butyrate used as a precursor is the one obtainable by the process of the invention.

One advantage of the present invention is that it provides a process for easily and cheaply obtaining α-keto butyrate by a biotechnological process. The resulting α-keto butyrate may easily and safely be used in food products or, which may be further processed to substances suitable for addition to food products. Generally, the α-keto butyrate produced according to the present invention is produced by a food grade micro-organism so that is safe for use in food products or for producing additives for food products.

BRIEF DESCRIPTION OF THE DRAWINGS

Additional features and advantages of the present invention are described in, and will be apparent from, the description of the presently preferred embodiments, which are set out below with reference to the drawings in which.

DETAILED DESCRIPTION OF THE PREFERRED EMBODIMENTS

Figure 1:
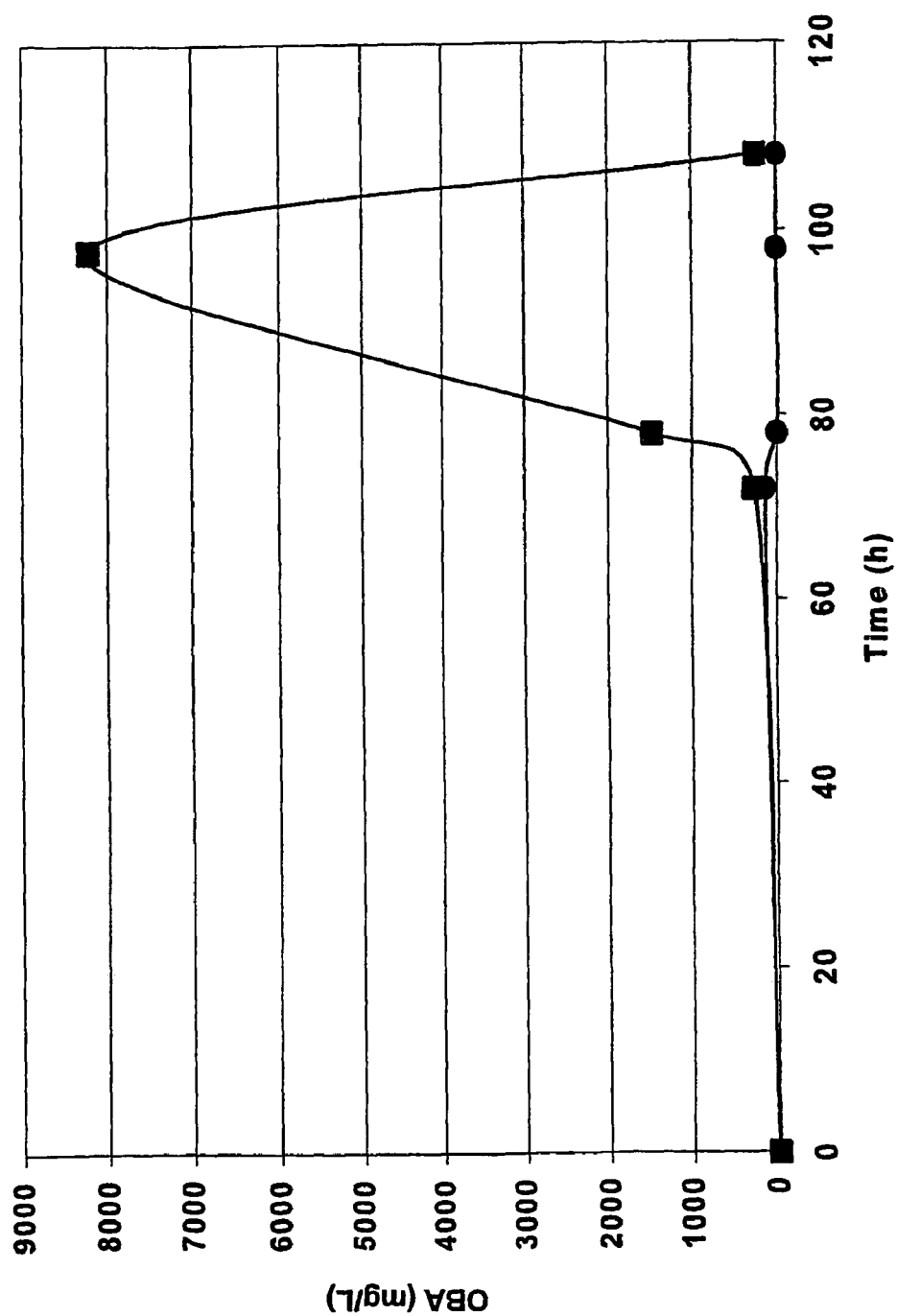
FIG. 1 shows the accumulation of α-keto-butyrate (OBA=oxo butyrate) in mg/L of fermentation medium over time (hours). The two curves illustrate a two step fermentation process, wherein the biomass of the micro-organism is transferred to a second medium suitable for accumulation of OBA after 72 hours of fermentation in a first medium. The lower of the two serves as a control (no threonine was added to the medium).

Initially, it is noted that the term α-keto-butyrate is substitutable by the synonymous name 2-oxo-butyrate or by the name of the corresponding conjugate acids.

The expression "natural mutant" is taken to refer to a mutant micro-organism, which was obtained by other means than by genetic engineering. In other words, the expression refers to a non-GMO (genetically modified organism).

Mutation, in the context of the present invention, should not be construed as a single point mutation, or a mutation only present on the coding region of a specific gene. Much to the contrary, a mutation is thought to be any kind of DNA alteration, at any locus that impacts the activity of the specific gene product mentioned in the context of the mutation. For example, an ilv-3 mutation (a locus in *Neurospora crassa*) should not be considered only as a mutation restricted to the coding region of the ilv-3 gene.

The term "linkage group", as used in "linkage group IV", is a term used in genetics and refers to a region on a chromosome with different loci, which tend to be inherited together.

The term "linkage group IV" refers to a chromosomal region of *N. crassa*, which incorporates the ilv-3 locus. For more detail: see Kuwana H, and Wagner R P, The iv-3 Mutants of *N. crassa*, I. Genetic and Biochemical Characteristics, Genetics 62: 479–485, 1969.

The ilv-3 gene, in the context of the present invention, is intended to mean the gene coding for EC 4.1.3.18 (Enzyme Commission number). Ilv-3 is the name of the gene in *N. crassa*. However, the term is herein considered to also include the same function of other organisms, for example in *Saccharomyces cerevisiae*, where it is known under the abbreviation ILV-2.

The EC numbers used herein refer to the enzyme classification system established by the International Union of Biochemistry and Molecular biology (IUBM).

Within the context of the present invention, the expressions "different" medium is not intended to be restricted to a completely different or new medium. It is however intended to mean that a medium is used, that is adjusted to a specific function, which is different from the function of one of the preceding media. The adjustment may be made by addition of nutrients, change of pH or total medium replacement, for example. Hence, the term "different" medium is substitutable by the term "modified" or "second" medium, depending on the context.

In an advantageous embodiment of the process according to the present invention, the micro-organism is a food grade micro-organism. Preferably, it is a bacterium, fungus or yeast, and more preferably, the micro-organism is a bacterium or a fungus. A suitable fungus is one belonging to the phylum of the *Ascomycota*, more preferably to the Subclass of the *Sordariomycetidae* and even more preferably to the order of the *Sordariales*. Suitable micro-organisms belong to the genus of *Neurospora* or is a *N. crassa* strain.

Advantageously, the micro-organism is a natural mutant micro-organism, such as one that has a mutation that impacts the isoleucine, leucine or valine biosynthetic pathways. Preferably, it is a mutant of the linkage group IV of *N. crassa*. For example, the natural mutant is an iv-3 mutant. The natural mutant strain may be selected from the strains cited in Kuwana H and Wagner R P, "The iv-3 mutants of *N. crassa*, I. Genetic and Biochemical Characteristics", Genetics 62: 479–485, 1969.

A *N. crassa* strain that is commercially obtainable from the Fungal Genetic Stock Center of the Kansas Medical Center, (Fungal genetics Stocks Center), is catalogue number FGSC 575, with the following characteristics: Mating type A, Genotype ilv-3, Alleles Y7110, Linkage group IVR, genetic background L, Mutagen M., markers: isoleucine plus valine-3. References: Barrat et al, 1954, Adv Genet 6:1–93. Perkins et al, 1969, Genetica 40:247–278. This strain has a mutation on the ilv-3 gene. Thus, in a preferred embodiment of the invention, the natural mutant comprises a malfunctioning, defect or inhibited ilv-3 gene-product and/or a mutation in the ilv-3 gene.

It is desirable for the micro-organism to exhibit very low or no acetohydroxy acid synthetase activity. When this is desired, the micro-organism may have a deficient or inhibited dehydroxy acid dehydratase or acetohydroxy acid synthase.

The process according to the present invention may encompasses one, two or more steps. If it encompasses two or more steps, there should be at least one step wherein biomass of the micro-organism is produced and at least one other step, wherein α-keto-butyrate is accumulated. The process may be a two or more step continuous or discontinuous fermentation. In a preferred embodiment, the process of the present invention comprises cultivating the micro-organism in a first medium which favors biomass production and enzyme activation, and thereafter cultivating the biomass in a different medium which favors accumulation and/or excretion of α-keto-butyrate. After the production of the biomass, the first medium is filtered, the residue (i.e., the micro-organism) is collected and transferred into a different medium. Alternatively, the medium may be modified to form a different medium in the presence of the micro-organism, that is, without a filtering step.

In a preferred embodiment, the medium, which favors the accumulation of α-keto-butyrate (for example, the second medium) comprises, in percent by weight, 0 to 1% valine, 0.1 to 10% threonine, and an accumulation favoring pH, such as one that is adjusted to 7–14. Preferably, the medium comprises 0.2 to 5% threonine.

The first medium may be a chemically defined medium which favors the biomass build-up and the appropriate enzyme activation, while the second or different medium comprises additional valine (as an enzyme trigger) and/or threonine (as a precursor). The first and the second media generally have a different pH due to these differences.

The process further comprises extracting, isolating and/or purifying α-keto-butyrate from the fermentation medium. For example, it may be isolated from the medium on a column with a suitable resin or by HPLC. In an alternative embodiment, α-keto-butyrate is only pre-purified, meaning that the medium containing α-keto-butyrate is used directly for further processing after only an incomplete, partial isolation. For example, the medium may just be filtered to remove the micro-organism and used directly for further processing. This approach may be successful, if emoxyfurone or sotolon (top-note flavors) are the end product. Emoxyfurone or sotolon may easily be isolated after synthesis has been completed.

In order to work the present invention, a suitable strain must be determined. Such a strain may be selected according to features of its metabolism. Usually, the bioconversion of threonine to α-keto-butyrate is common in most organisms, including animals, higher plants and unicellular organisms. Therefore, a suitable strain may be selected from a huge number or organisms. Preferably, a micro-organism or cell-line is selected that, in case of the wild-type, is possesses the ability to convert α-keto-butyrate to 2-aceto-2-hydroxy-butyrate. In other words, a micro-organism that is capable of synthesizing isoleucine and/or valine and leucine, if present as wild-type. This requirement holds true for higher plants and many unicellular organisms. Any kind of these organisms may be suitable to accumulate α-keto-butyrate if the valine or isoleucine pathway is somehow negatively affected.

For example, a strain is selected that accumulates or excretes α-keto-butyrate because of a deficient, malfunctioning or inhibited acetohydroxy acid synthase (the enzyme is given the Enzyme Commission number EC 4.1.3.18), which is capable of converting α-keto-butyrate to α-aceto-2-hydroxy-butyrate in wild-type organisms as those mentioned above. The enzyme, also called aceto lactate synthetase, owes the latter name to its parallel ability to convert pyruvate to α-acetolactate. Hence, a strain may be selected, in which this enzyme is inhibited, deficient, malfunctioning or simply not expressed. For example, a natural mutant may be used, in which a mutation in the gene encoding this enzyme or in transcription factors involved in its expression prevents normal functioning of the corresponding enzyme.

Of course, also other mutants will be capable of accumulating α-keto-butyrate. Especially, strains that comprise one or several mutations affecting the biosynthetic pathway of the amino acids valine, isoleucine and leucine may be useful. For example, strains with a deficient acetohydroxy acid reductoisomerase (EC 1.1.1.86), dihydroxy acid dehydratase (EC 4.2.1.9) or branched-chain amino acid transaminase (EC 2.6.1.42), and so forth, may be selected for ability to accumulate α-keto-butyrate and hence, may be suitable strains according to the invention. However, also other mutants may accumulate α-keto-butyrate.

For example, a fungal strain is used, preferably selected from the subdivision of the ascomycotina. Specific bacteria may instead be suitable. For example, a yeast strain may be used. A strain from the genus of *Neurospora,* in particular from the species *N. crassa,* is preferably used. In an embodiment of the invention, the *N. crassa* strain from the University of Kansas Medical Center mentioned above is used. This specific strain was already described as Y7110-strain in: Kuwana and Wagner, The iv-3 mutants of *N. crassa,* I. Genetic and biochemical characteristics, genetics 62: 479–485, 1969. Generally, a food-grade micro-organism is preferred.

In order to obtain α-keto-butyrate, a suitable medium must be selected. Depending on the selected strain, also a preculture may be prepared. In general, the choice of an optimal medium, for preculture or main fermentation as well as all fermentation parameters depends highly on the selected strain. The skilled person usually is aware of the optimal growing or cultivating conditions of specific strains.

For example, if a fungus such as *N. crassa* is used, it may be adequate to obtain a suspension of spores as a starter material, which will allow a synchronized and rapid biomass production at a later stage of the process. For most fungal strains, the specific fermentation parameters (temperature, pH, light, nutritional supply) that favor sporulation are generally known. For example, in *N. crassa* strains, the so called Horowitz-medium (agar) may be used (see: Deutsch, "Das Experiment: Sporenmusterbildung beim Schlauchpilz *N. crassa*", Biologie in unserer Zeit, 1993, 23(4): 259–264). *N. crassa* strains are streaked onto agar-Erlenmeyer and grown under light at 25° C. for 120 hours. In general, conditions are selected that are known to favor spore formation, sexually or asexually produced ones. As soon as sufficient biomass has been built up, sterile water may be added to the agar plate, which suspends the spores if shaken lightly. The spore suspension thus obtained may be used as a starter culture. In case that bacteria or cell-lines are selected to carry out the invention, the starter has to be prepared differently, taking into account the peculiarities of the specific bacterial strain or cell-line.

The starter culture may be used to inoculate a medium, which favors vegetative growth, biomass production and/or accumulation of α-keto butyrate without or with reduced spore formation. If *N. crassa* is selected to carry out the invention, for example, the starter may be added to a liquid medium, such as a Vogel-Saccharose medium, as described earlier (Deutsch, "Das Experiment: Sporenmusterbildung beim Schlauchpilz *N. crassa*", Biologie in unserer Zeit, 1993, 23(4): 259–264). On a lab-scale, the spores may be added to liquid medium in an Erlenmeyer flask, which is maintained at a temperature of 25° C. and shaken or mixed with a stirrer at 100–200 rpm.

After starting the fermentation, for example 8 to 40 hours after inoculation and preferably 8 to 30 hours after inoculation, threonine may be added to the medium to achieve a concentration of 0.1 to 5% threonine in percent by weight. A preferred concentration is 0.2 to 4%, and more preferably is 0.5 to 3% threonine per liter of medium.

If a strain with a deficient aceto lactate synthetase is used, isoleucine and valine may also be added to the medium, because the strain cannot synthesize these amino acids. Of course, the same holds true for any strain with any mutation or deficiency affecting the isoleucine/valine pathway. However, these amino acids should be added in finely tuned amounts, because of negative or positive feedback regulation mechanisms. In particular, high levels of isoleucine inhibit or down-regulate the activity of the threonine dehydratase (ilv-1 gene product in *N. crassa*) and, hence, reduce the accumulation of α-keto-butyrate. Interestingly, valine, which is an activator of the ilv-1 gene product of *N. crassa,* should not be added in ample amounts. Accordingly, valine is added to the medium in an initial amount of 0.005 to 1.5% by weight of total medium. Preferably, valine is added to the medium in an amount of 0.01 to 1%, and more preferably 0.01 to 0.5% by weight.

The fermentation time, however, depends on the type of fermentation that is conducted. The accumulation of alpha keto butyrate in the medium fermented by the *N. crassa* described above may reach a high amount after an optimal time of fermentation. The maximum amount may be achieved after 20 to 200 hours, preferably 40 to 150 hours after starting the fermentation.

The cultivation of biomass for obtaining α-keto-butyrate as depicted above is usually referred to as a continuous fermentation process. For example, no substances at all need be added to the medium after fermentation has started. In the same line, threonine, or nutrients may be added after a certain time only, for example after 10 to 40 hours after inoculation of the medium. According to another variation, threonine is added in different intervals after start of the fermentation, for example after 8, 16, 24, 48 and 72 hours. Additionally, other metabolites or nutrients may be added according to such a pattern.

Continuous or batch processes with transient properties as described above are generally characterized in that the formation of biomass is achieved substantially simultaneously to the accumulation of the key-metabolite. Concomitantly, besides the usual pH drop during fermentation, no drastic change in pH may be effected.

Alternatively, a more sophisticated continuous two (or more) step process may be applied. This kind of fermentation yields, as was found surprisingly, much higher concentrations of α-keto-butyrate, because the medium composition is optimized to a specific effect of a specific step. For example, it is possible to envisage a first step, which is directed to build up biomass, and a following step, for example, a second step, where essentially the bioconversion occurs.

The two (or more) step fermentation process, surprisingly, proved to be especially suitable for the accumulation of α-keto-butyrate. Two approaches may be followed. First, a continuous two step fermentation process may be conducted. Accordingly, biomass may be produced at a specific pH. As soon as sufficient biomass has been built up (0.01 g wet weight/ml, for example), the pH (or another, strain specific parameter) is changed and, optionally, further medium ingredients are added without discarding the original medium.

Of course, depending on the selected micro-organism that is used, pH and other parameters may differ drastically. In particular, optimal pH for biomass formation and α-keto butyrate synthesis may be different from the values given below. It is even possible, that a strain has the same or a similar optimal pH for both steps, the biomass formation and the α-keto butyrate synthesis.

If α-keto-butyrate is to be produced with the *N. crassa* strain described above, the starting pH for the accumulation of biomass should be below 7, preferably 4 to 6, more preferably 4.5 to 6. At this pH range and a temperature of 20 to 30° C., the fermentation is started and conducted for 1 to 10 days, preferably 2 to 5 days, for example with the Vogel-saccharose medium indicated above and under agitation or stirring.

When sufficient biomass is built up, the pH may be increased to 7 to 14, and preferably 9 to 11 by addition of a base such as NaOH, thus starting the bioconversion process. Furthermore threonine, valine and/or isoleucine may be added at this stage.

According to this process, 2 to 10 g α-keto-butyrate per L medium may be produced by the *N. crassa* strain identified above. In addition, the process is simple and rapid, because the pH change is essentially sufficient to start increased α-keto-butyrate synthesis.

On the other hand, a discontinuous two step approach is also possible in the context of the present invention. Accordingly, after the biomass is built up, it is separated from the medium, for example by filtration. Thereafter, the biomass is put into a new medium, which is adjusted to the promotion of accumulation of α-keto-butyrate.

In case that a fungal *N. crassa* strain is used to accumulate α-keto-butyrate, the pH of the medium to promote accumulation thereof has a pH of 7 to 14, preferably 9 to 11. Like the continuous two step approach, this process yields high amounts of α-keto-butyrate (3–10 g/L). It is possible that by further specific adjustments of the medium even higher concentrations are obtained.

For example, the biomass formation may be conducted in a Vogel-saccharose medium also used for the continuous two step approach. The biomass build-up may be conducted at 10° C. to 45° C., preferably 22 to 30° C. for 1 to 7 days, preferably 1 t days, under slight agitation or stirring, for example.

For the bioconversion, the biomass may be separated, for example by filtration, from the first medium suitable for producing biomass and, for example, put into a buffer suitable for bioconversion. Such a buffer or medium is generally characterized by a pH and amino-acid concentrations that favor the accumulation of the target molecule. The skilled person is aware of the factors to be added to the medium and the parameters to be adjusted to this end. The factors are generally chosen in a way that the enzymes implied in the desired bioconversion are activated.

For example, if the *N. crassa* strain defined above is used, a phosphate buffer (0.1 M) or glycine buffer (0.1 M) with pH 7–14, preferably, 9 to 11 may be used. The buffer may be supplemented with threonine, for example, 0.1 to 10%, preferably 0.1 to 5%, more preferably 0.2 to 4% and valine, for example, 0.005 to 1.5%, preferably 0.01 to 0.5%, to convert threonine into α-keto-butyrate. The fermentation in the phosphate buffer for bioconversion may be conducted for 12 hours to 3 days, preferably 18 hours to 48 hours, at a temperature of 10 to 45° C., preferably 23 to 30° C.

In general, the same starter and liquid medium and the same additional supplements of specific amino acids as described for the continuous one-step process set out above may be used.

Of course, instead of conducting fermentation with an intact micro-organism, an enzyme extract of such or a commercially available enzyme isolate may be used to perform the bioconversion from threonine to α-keto-butyrate. For example, enzymes may be extracted from the *N. crassa* strain referred to herein. A medium comprising an optimized pH, enzyme activators and precursors is then prepared to accumulate α-keto-butyrate.

Depending on the further utilization of the α-keto-butyrate, it may be isolated from the medium, for example on a column with a suitable resin or by HPLC. When the α-keto-butyrate is to be used as an intermediate to synthesize other end-products, for example, flavors such as emoxyfurone (5-ethyl-3-hydroxy-4-methyl-2(5H)-furanone) or sotolon (3-hydroxy-4,5-dimethyl-2(5H)-furanone), a purification or isolation process may be adequate. These two flavors generally constitute "top-notes", which are used in very low concentrations. Emoxyfurone may be produced by filtering the fungal hyphes from the medium, optionally further purifying the medium and by changing the conditions to promote a lactonization reaction.

In a first step, it may be adequate to determine the concentration of α-keto-butyrate in the medium. Addition of $K_2CO_3$ to the medium in the same concentration of α-keto-butyrate favors the formation of the enol tautomer of α-keto-butyrate. Thereafter, pH may be adjusted to 8 and phosphate buffer may be added. Then the medium is heated, such as for 4 hours at 120° C. Optionally, boiling stones may be added at this stage to prevent boiling over of the medium. In this step, emoxyfurone (5-ethyl-3-4-methyl-2(5H-furanone) is formed, consisting of originally two molecules of α-keto-butyrate, one of them in the enol-form. Thereafter, the medium may be cooled to under 10° C. and 10% HCl is added (10 parts of 10% HCl per part of α-keto-butyrate). Subsequently, the medium may be heated again for ½ to 3 hours to alleviate ketone hydrolysis. Ring formation may be finally achieved by applying a vacuum (10 to 100 mbar) at 40 to 90° C., which leads to water and (½) $CO_2$ split of from the molecule, which results in emoxyfuran.

Emoxyfurone (a lactone) then may be easily isolated from the medium by ether extraction, for example by using methyltetrabutylether in 3 cycles in a $H_2O$ system and with addition of sodium sulfate.

EXAMPLES

The following examples are given by way of illustration only and in no way should be construed as limiting the subject matter of the present application. Percentages and parts are by weight unless otherwise indicated.

Example 1

Accumulation of α-keto-butyrate by Bioconversion of Threonine in *N. crassa*

Material and Methods

Spores of a *N. crassa* strain with a ilv-3 (−) genotype purchased from the Kansas Medical Center under catalogue number FGSC 575, mating type A, are plated out on agar in an Erlenmeyer for preparation of a starter. The composition of the "Horowitz"-medium, which is used to this end, is given in table 1 below.

TABLE 1

"Horowitz" medium for cultivation of *N. crassa* to obtain spores.

| Ingredient | Amount per liter |
| --- | --- |
| Whole Salt Solution* | 200 ml |
| Glycerol (87%) | 185 ml |
| Casein hydrolysate | 0.5 g |
| Yeast Extract | 5 g |
| Malt Extract | 5 g |
| Agar | 20 g |
| Biotin Solution** | 100 μl |
| Distilled water | adjust to 1000 ml |
| pH | 6.5 |

*Whole Salt Solution
25 g K-Tartrate (di-Potassium tartrate hemihydrate - Merck)
20 g Na-Nitrate
5 g $KH_2PO_4$
2.5 g $MgSO_4 \times 7H_2O$
0.5 g $CaCl_2 \times 2H_2O$
0.5 g NaCl
Adjust to 1000 ml with distilled water.
**Biotin Solution
Dissolve 5 mg Biotin in 100 ml 50% Ethanol.

The strain is grown under light at 25° C. for 120 hours.

Thereafter, 10 ml of distilled water are put into the Erlenmeyer to suspense the spores. 4 ml of the suspension are taken and put into an Erlenmeyer containing liquid "Vogel-saccharose"-medium, given in table 2 below. This medium is enriched, from the beginning, with L-valine and L-isoleucine. Furthermore, the "Vogel-saccharose-medium comprises a modified "Vogel-salt solution", the ingredients of which are given in table 3 below. Fermentation is conducted at 25° C. and 100 rpm for 168 hours (7 days). L-threonine is added 24 hours after the start of the fermentation (10 g/l).

TABLE 2

"Vogel-saccharose" medium for fermentation of *N. crassa*

| Ingredient | % |
| --- | --- |
| Modified Vogel-Salt solution | 2 |
| Saccharose solution (50%) | 2 |
| L-Valine solution (25 g/l)* | 0.07 |
| L-Isoleucine solution (25 g/l)* | 0.03 |
| L-Threonine (100 g/l) | 2 |
| Sterile water | 93.9 |

TABLE 3

Modified "Vogel-salt" solution as used in the "Vogel-saccharose" fermentation medium.

| Ingredient | Amount per liter |
| --- | --- |
| $C_6H_5NaO_7 \times 5\ H_2O$ | 150 g |
| $KH_2PO_4$ | 250 g |
| $NH_4NO_3$ (modification) | 0 |
| $MgSO_4 \times 7\ H_2O$ | 10 g |
| $CaCl_2 \times 2\ H_2O$ (to 20 ml $H_2O$ dissolve) | 5 g |
| Biotin Solution (see table 1) | 5 ml |
| Trace element solution*** | 5 ml |
| Distilled water | adjust to 1000 ml |

***Trace element solution
5 g citric acid × $H_2O$
5 g $ZnSO_4 \times H_2O$
1 g $Fe(NH_4)_2(SO_4)_2 \times 6\ H_2O$
0.25 g $CuSO_4 \times 5\ H_2O$
0.05 g $MnSO_4 \times H_2O$
0.05 g $H_3BO_3$
0.05 g $Na_2MoO_4 \times 2\ H_2O$ (Sodium molybdate dihydrate - Merck)
Adjust to 100 ml with distilled water.

Samples of the medium are taken after 24, 48, 72 hours and analyzed for by HPLC (high performance liquid chromatography).

Results

In the medium, α-keto-butyrate accumulated up to 400 mg/l (HPLC-analysis).

In conclusion, by fermentation of a natural mutant microorganism it is possible to achieve an accumulation of α-keto-butyrate in the medium. In the present example, a natural ilv-3 mutant ascomycotine fungus (*N. crassa*) proved to be effective.

Example 2

Increased Accumulation of α-keto-butyrate in a Two-Step Fermentation Process

Material and Methods

The same strain, media and equipment as cited in example 1 are used.

In a first fermentation, biomass is produced by inoculating a medium comprising the enriched Vogel-salt solution, L-valine and L-isoleucine (threonine is added lately) according to the data in example 1. At the beginning of the fermentation, the pH is at 5.8, and drops to 4.4 after 72 hours at 26° C. under slight agitation (200 rpm).

Then the hyphal cells are filtrated (0.22 μm) and transferred into a different medium, that is a phosphate buffer (0.1 M), which further comprises threonine (2%) and valine (0.03%). The pH is adjusted to 10 with NaOH (10N).

After in total 110 hours, at 25° C. and 200 rpm, the bioconversion is interrupted by filtrating the medium to remove the biomass and storing the permeate at 4° C. until further analysis.

Results

High amounts of α-keto-butyrate (>8 g/l) were obtained in the medium after conducting a two-step fermentation with *N. crassa*. FIG. 1 illustrates the accumulation of α-keto-butyrate during time of the overall fermentation process. Bioconversion of threonine to α-keto-butyrate was up to 90%.

In conclusion, the two-step fermentation of a suitable medium with a natural mutant food-grade micro-organism yields sufficient amounts of α-keto-butyrate converted from threonine to enable a industrial production.

What is claimed is:

1. A process for accumulating α-keto-butyrate by bioconversion from threonine by a food grade micro-organism cultivated in a fermentation medium, wherein the micro-organism is selected from the strain *Neurospora crassa*.

2. The process according to claim 1, wherein the micro-organism is a natural mutant micro-organism.

3. The process according to claim 1, wherein the micro-organism exhibits no acetohydroxy acid synthetase activity.

4. The process according to claim 1, which further comprises cultivating the micro-organism in a first medium which favors the production of biomass of the micro-organism, and thereafter cultivating the biomass in a different medium which favors accumulation or excretion of the α-keto-butyrate.

5. The process according to claim 4, wherein the medium which favors accumulation or excretion of the α-keto-butyrate comprises, in percent by weight, 0.1 to 10% threonine, 0 to 1% valine, and a pH that is adjusted to 7–11.

6. The process according to claim 1, which further comprises extracting, isolating or purifying the α-keto-butyrate from the fermentation medium.

7. The process according to claim 6, wherein the α-keto-butyrate is recovered from the fermentation medium in an amount of >8 g/l.

* * * * *